(12) United States Patent
Agarelli et al.

(10) Patent No.: US 8,563,016 B2
(45) Date of Patent: *Oct. 22, 2013

(54) LAMELLAR OIL-IN-GLYCOL GEL COMPOSITIONS AND THE PROCESS OF PREPARATION

(75) Inventors: Alexandra Bazito Agarelli, Sao Paula (BR); Yan Zhou, Montville, NJ (US); Nelson Luis Perassinoto, Campinas (BR); Maria Regina Bartuccio Raponi, Sao Caetano Do Sul (BR); Ligia Vairoletto, Sao Paulo (BR); Liliana Calore Brenner, Sao Paulo (BR)

(73) Assignee: ISP Investments Inc., Wilmington, DE (US)

( * ) Notice: Subject to any disclaimer, the term of this patent is extended or adjusted under 35 U.S.C. 154(b) by 790 days.

This patent is subject to a terminal disclaimer.

(21) Appl. No.: 11/913,471

(22) PCT Filed: Apr. 28, 2006

(86) PCT No.: PCT/US2006/016317
§ 371 (c)(1),
(2), (4) Date: Jul. 24, 2008

(87) PCT Pub. No.: WO2006/119042
PCT Pub. Date: Nov. 9, 2006

(65) Prior Publication Data
US 2009/0142381 A1    Jun. 4, 2009

(51) Int. Cl.
*A61K 9/00* (2006.01)
*A61K 9/107* (2006.01)

(52) U.S. Cl.
USPC ........... 424/401; 424/70.1; 514/553; 514/937

(58) Field of Classification Search
USPC .......................... 424/401, 70.1; 514/553, 937
See application file for complete search history.

(56) References Cited

U.S. PATENT DOCUMENTS

| | | | |
|---|---|---|---|
| 6,342,238 B1 * | 1/2002 | Simonnet et al. | 424/401 |
| 6,565,884 B2 * | 5/2003 | Nimni | 424/484 |
| 7,374,750 B2 * | 5/2008 | Albano | 424/70.1 |
| 2004/0067244 A1 * | 4/2004 | Friedman | 424/401 |

FOREIGN PATENT DOCUMENTS

| | | |
|---|---|---|
| EP | 1547574 | 6/2005 |
| WO | 99/62462 | 12/1999 |
| WO | 00/56346 | 9/2000 |
| WO | 01/19343 | 3/2001 |
| WO | 02/24152 | 3/2002 |

OTHER PUBLICATIONS

"Use of disodium lauriminodipropionate tocopheryl phosphates as an antiinflammatory and moisturizer in infant, e.g., diaper, and adult care", Derwent Acc. No. 2006-811204, Sep. 10, 2003, RD473020A, abstract.*
Supplementary European Search Report issued regarding European Application No. 06758760.0 (Jun. 6, 2008).

* cited by examiner

*Primary Examiner* — Gina C Justice
(74) *Attorney, Agent, or Firm* — Thompson Hine LLP; William J. Davis

(57) ABSTRACT

The present invention is directed to a lamellar oil-in-glycol gel comprising (a) at least one glycol, (b) at least one fatty alcohol, (c) at least one cationic surfactant and optionally (d) at least one benefit agent, said lamellar gel capable of providing enhanced mass and promoting the permeation of the benefit agent through a keratinous substrate such as the skin, hair and fingernails, providing both deep and superficial treatment thereof.

16 Claims, 4 Drawing Sheets

Test of wet combability

A- Control
B- 1 Treatment
C- Treatment + washing
D- 5 Treatments

Test of wet combability with 72 hours of exposure to the solar radiation

A- Treated + 72 hours of irradiation
B- Control

FIG. 4A

Treatment of the capilar fiber external surface area
Microscopy fluorecence essay of the longitudinal segment

sample treated with control shampoo (10% LESS)

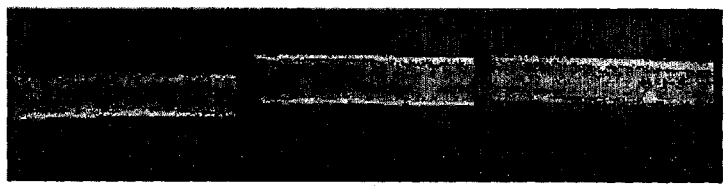

sample treated with control shampoo (10% LESS) + lamellar gel

FIG. 4B

Treatment of the capilar fiber cortex
Microscopy fluorescence essay of the sectional segment

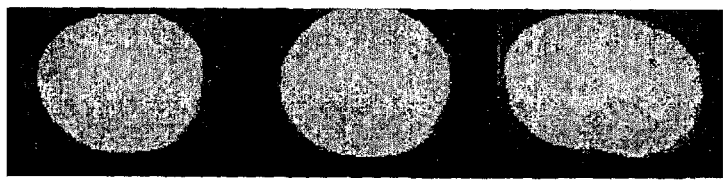

sample treated with control shampoo (10% LESS)

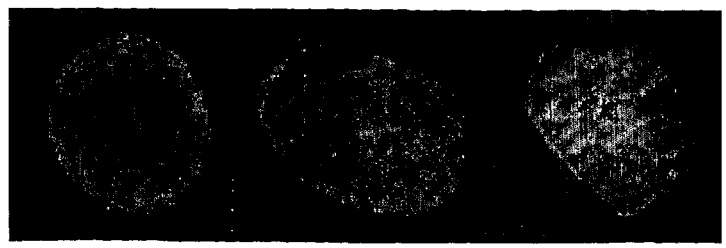

sample treated with control shampoo (10% LESS) + lamellar gel ns of the amino acid cystein and is responsible for providing protection to the external layers of the skin, hair and fingernails.
LAMELLAR OIL-IN-GLYCOL GEL COMPOSITIONS AND THE PROCESS OF PREPARATION

DISCLOSURE OF THE INVENTION

The object of the present invention is a lamellar oil-in-glycol gel comprising (a) at least one glycol, (b) at least one fatty alcohol, (c) at least one cationic surfactant and optionally (d) at least one benefit agent, said lamellar gel being capable of providing enhanced mass and promoting the permeation of the benefit agent through a keratinous substrate such as the skin, hair and fingernails, providing both deep and superficial treatment thereof.

BACKGROUND OF THE INVENTION

Keratin ($SCH_2CH(NH_2)COOH$) is a fibrous protein that is composed of several units of the amino acid cystein and is responsible for providing protection to the external layers of the skin, hair and fingernails.

The epidermis, the external layer of the skin, is divided in four portions. The outermost one, which is known as stratum corneum, is made up of dead cells and keratin and constitutes the major physical barrier to the penetration of topical use compositions. In general, hair and fingernails are also composed of keratin.

The human hair, for example, has a complex structure that consists of three distinct morphological components, its primary element being the keratin that corresponds to at least 65% of the hair fiber. The central core of the fiber is known as medulla. It is surrounded by the cortex, a layer composed of keratinized cells, that provide every fiber with mechanical strength. The outermost layer is the cuticle, a fine layer of juxtaposed keratinized scales that acts as a protective barrier.

The amino acid cystein that is present all over the extension of the keratin polymer, contains sulfur. Through oxidation, two molecules of cystein can provide strong disulfide links and, thus, bind adjacent keratin polymers. Such cystein links contribute to the strength of the hair and are responsible for its durability and resistance.

Daily, the keratinous substrata, mainly the hair, are exposed to several kinds of stress. Some of them are induced by environmental factors, such as UVA and UVB radiation, or by mechanical treatments using combs, brushes, heat drying devices, among others. Also, there is the stress caused by chemical processes in the form of dyes, permanents, smoothing and discoloration. These processes not only destroy the cystein links (disulfide bridges), but also cause the loss of proteins, loss of hydration, premature aging, hardness, fragility, rupture of fibers, and the like (as per "Chemical and Physical Behavior of Human Hair", Fourth Edition, Clarence R. Robbins).

Compositions for the care of keratinous substrate are known, but such compositions are not capable of providing, simultaneously, superficial as well as deep care to said substrata. A number of patent documents disclosing care compositions of keratinous substrata are given below, some formulated in the lamellar phase, but they neither indicate nor suggest simultaneous superficial and deep care.

The international patent application WO99/44564 discloses a composition in the form of a micro-emulsion for treating keratin fibers that comprises UV absorbers. Application WO93/15709 discloses a prophylactic composition containing an oleophilic liquid vehicle that promotes the diffusion of reagents in keratinous materials.

Application WO99/62462 discloses a composition for the repair and prevention of damage to the hair fiber that comprises a dispersion of multilamellar vesicles formed as a mixture of cholesterol and amino acids, and fatty acid.

U.S. Pat. No. 6,342,238 discloses a composition for stabilizing oxidation sensitive compounds that comprises an oily phase in a glycerol phase, and a non-ionic surfactant, said compound being dispersed in the glycerol phase.

Most of the available lamellar compositions comprise water, for example forming structures of the oil in water type, which makes it difficult to attain deep care, resulting only in superficial care of keratinous substrata.

The compositions that provide deep care of keratinous substrata are still more difficult to be obtained, mainly for keratinic fibers, including hair, body hair, eyebrows, eyelashes, mustache, beard, among others.

Some compositions that act as a vehicle for the transdermal administration of actives also can be found, but such compositions act as a vehicle in the transport of actives through the whole extension of the skin and are not suitable for the superficial treatment thereof.

For example, the international patent application WO02/24152 describes a pharmaceutical or cosmetic composition in the form of a micro-emulsion of vegetable oil in glycerin that comprises at least one emulsifier selected among glycosides, sucrose esters or sorbitan and a bioactive component of a hydrophobic moiety. The composition makes it easier for the bioactive agent to penetrate the stratum corneum and dermis and its diffusion in the blood stream, resulting in a systemic effect via transdermal route.

Thus, there remains the need of a composition that makes it possible to attain the simultaneous superficial and deep repair of damages suffered by keratinous substrata.

BRIEF DESCRIPTION OF THE DRAWINGS

FIGS. 4A-B show fluorescence microscopy photographs of samples treated with a lamellar gel composition according to one embodiment, of longitudinal segments (A) and sectional segments (B).

DISCLOSURE OF THE INVENTION

Figure 1A:
FIGS. 1A-B show optical microscope photographs using polarized light of a lamellar gel composition according to one embodiment.

We have discovered in particular that the permeation of certain benefit agents in keratinous substrata can be particularly increased when such agents are formulated as a lamellar gel system of the oil in glycol type, having a melting point below about 46° C.

In addition, compositions of this nature not only convey the benefit agent through the keratinous barrier, but are also capable of acting in all the phases of the barrier layer, providing both superficial and deep care, besides preventing the main symptoms of damages suffered by the keratinous substrate.

Thus, the present invention provides, for both superficial and deep care of keratinous substrata, a lamellar oil-in-glycol gel that comprises (a) at least one glycol, (b) at least one fatty alcohol, (c) at least one cationic surfactant and optionally (d) at least one benefit agent.

In accordance with the present invention, by "superficial care" it is meant the performance of one or more benefit agents in the keratinous barrier layer, and by "deep care" it is meant the effect of one or more benefit agents permeated through the barrier keratinous layer as far as the inner layers. By "superficial and deep care" it is meant the simultaneous performance of the benefit agents both in the barrier and inner layers.

Keratinous substrata comprise, without being limited thereto, the skin, fingernails and hair in general, such as hair, eyebrows, eyelashes, mustache, beard and other hair of the human or animal body, or also synthetic substrata.

The glycols used in the lamellar gel of the present invention are those having at least two hydroxyls, such as butylene glycol or propylene glycol, preferably those having at least three hydroxyls, such as 1,2,3-propanetriol. A useful amount of glycol in the lamellar gel can range from about 30 to about 90%, preferably from about 40 and 70%, more particularly from about 45 to about 65% by weight, based on the total weight of the lamellar gel.

The fatty alcohols that can be used in the lamellar gel described herein comprise compounds having the general formula $RCH_2OH$, wherein R is a saturated or unsaturated hydrocarbon radical having an average of from 5 to 27, preferably from 10 to 22 carbon atoms, of linear or branched chain.

Suitable fatty alcohols are those having branched chains, such as isocetyl alcohol, those having linear chains, such as stearyl, cetyl or behenic alcohol and the unsaturated ones, such as the oleic or linoleic alcohol. The fatty alcohols can be used individually or in the form of mixtures.

A suitable amount of fatty alcohol in the lamellar gel of the present invention ranges from about 0.1 to about 40%, preferably from about 0.5 to about 35%, and more preferably from about 3 to about 22% by weight, based on the total weight of the composition.

Cationic surfactants that can be used in the present invention can comprise all those that are capable of forming a lamellar gel structure, in particular quaternized surfactants. The preferred quaternized cationic surfactants in accordance with the present invention are the quaternary ammonium compounds of general formula $(R,R',R'',R''' N)^+ X^-$, wherein R, R', R'' and R''' are identical or different and wherein $X^-$ represents an anion, for example, chloride. The group R can be aliphatic or carry additional substitutes, and N can be part of a heterocyclic or aromatic ring.

In the most preferred quaternized surfactants, R and R' are $CH_3$, and R'' and R''' are aliphatic or aromatic chains, for example, hydroxy ethyl cetearamidopropyldimmonium chloride, dimethylPABAmidopropyl laurdimmonium tosylate, quaternium 70, or mixtures thereof.

A suitable amount of cationic surfactant in the lamellar gel of the present invention ranges from about 0.001 to about 30%, preferably from about 0.01 to about 25%, and more preferably from about 0.2 to about 20% by weight, based on the total weight of the composition.

Benefit agents in accordance with the present invention include those capable of providing the keratinous substrata with a beneficial effect, such as conditioning, hydration, sun protection, protection against oxidative processes, restoration, among others. By "restoration" it is meant any direct or indirect reconstruction effect provided to keratinous substrata, such as strength, mass increase, elasticity, softness, combability, among others.

Preferred benefit agents include amino acids or amino acid mixtures, their salts, esters and acyl derivatives of the general formula $RCH(NH_2)COOH$, wherein R is an aliphatic hydrocarbon group such as glycine, a dibasic group such as lysine, or a group containing sulfur, such as N-acetyl cystein.

The amino acids can be alkyl substituted, their substituted salts and imino alkyl acids, preference being given their disodium salts derived from complex mixtures of esters, such as the phosphated derivatives, in particular disodium lauriminodipropionate tocopheryl phosphate.

A suitable amount of amino acids used in the lamellar gel of the present invention ranges from about 0.001 to about 20%, preferably from about 0.005 to about 10%, and more preferably from about 0.01 to about 6% by weight, based on the total weight of the composition.

A suitable amount of alkyl substituted amino acids substituted in the lamellar gel of the present invention can range from about 0.001 to about 30%, preferably from about 0.01 to about 15%, and more particularly from about 0.1 to about 6% by weight, based on the total weight of the composition.

Suitable benefit agents also include silicones or a mixture of silicones, preferably when emulsified with non-ionic emulsifiers, forming emulsified silicone particles. Particular non-ionic emulsifiers are alkoxylated alcohols, more particularly $C_{12-14}$ chain, for example, $C_{12-14}$ sec-pareth-5 or sec-pareth-7 and amines. In particular, silicones that can be used in the present invention comprise siloxane polymers terminated with functional amino groups, such as amodimethycone.

A suitable amount of silicone in the lamellar gel of the present invention ranges from about 0.001 to about 30%, preferably from about 0.01 to about 25%, and more preferably from about 0.02 to about 10% by weight, based on the total weight of the composition.

Preferably, the lamellar gel of the present invention is substantially free of water, that is, it can comprise a small amount of water such that the permeation profile of the lamellar gel is not substantially changed.

Another object of the present invention is a process for the preparation of a lamellar gel oil-in-glycol, which process comprises (1) heating individually at least one glycol and at least one fatty alcohol to a temperature of about 65° C. to about 85° C., preferably about 75° C., more preferably about 70° C., (2) adding the fatty alcohol to the glycol under agitation, (3) keeping the agitation until the mixture is homogenized, (4) cooling the homogenized mixture to from about 30° C. to about 50° C., preferably to about 40° C., and optionally (5) adding to it at least one benefit agent under agitation until a homogeneous product is obtained.

The pH of the finished article preferably can range from about 3.5 to about 5.5 and its viscosity can range from about 5,000 to about 1,000,000 cps.

The lamellar gel of the present invention can be used directly in the care of keratinous substrate, and also it can be used in compositions, formulations or mixtures with excipients compatible with the keratinous substrata for obtaining a cosmetic product, such as creams, ointments, pastes, emulsions, gels, combined cosmetic forms or the like.

Another technical advantage of the present invention is that the lamellar oil-in-glycol gel has a melting point below about 46° C., preferably from about 36° C. to about 46° C., and it does not require the task of intense agitation or whirl when used in the preparation of other cosmetic products.

Such characteristics provide savings in time, process and energy when the lamellar oil-in-glycol gel is used for the preparation of other cosmetic products.

Another object of the present invention is the use of the lamellar oil-in-glycol gel for simultaneous superficial and deep care of keratinous substrata, providing restoration, reduction and protection against the stress effects.

The examples below aim to illustrate the many aspects of the present invention without any limiting character. Mention is made to the application to hair only for facilitating the explanation, without however imposing a limitation to only this use.

EXAMPLES

Example 1

Preparation Process 62.5 g of 1,2,3-propanetriol was placed in a first suitable container and heated to 75° C.

In a second container, fatty alcohols were weighed, namely 3.5 g behenic alcohol, 3.5 g cetyl alcohol and 8 g isocetyl alcohol. Next, the quaternized surfactants were weighed in the same container, namely 3 g hydroxy ethyl cetearamidopropyldimmonium chloride, 5 g dimethylPABAmidopropyl laurdimmonium tosylate and 8 g quaternium 70.

The mixture of the second container was homogenized and heated to 70° C. and then was added under appropriate agitation to the first container.

The agitation was kept and the new mixture was cooled to 40° C.

Next, 0.4 g glycine, 0.4 g lauroyl lysine, 0.2 g arginine HCl, 0.2 g N-acetyl cystein, 3.8 g disodium lauriminodipropionate tocopheryl phosphate and 0.5 g amodimethicone were added under agitation and emulsified with 0.5 g $C_{12-14}$ sec-pareth-5 and 0.5 g $C_{12-14}$ sec-pareth-7, terminating the process.

Example 2

Formation of the Lamellar Gel System

Figure 1B:
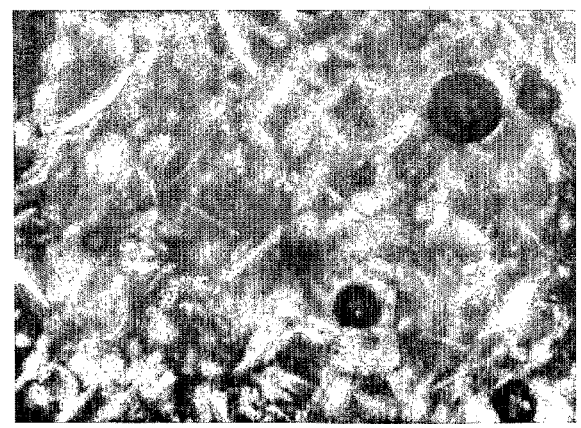

A sample of the composition prepared according to Example 1 was taken and examined in an optical microscope using polarized light, with 200× magnification, and the presence of three-dimensional components was observed, that is, the formation of a lamellar gel system. The result is shown in FIGS. 1A and 1B.

Example 3

Comparative Test of Wet Combability in Standardized Discolored Hair Tufts

A sample of the composition disclosed in Example 1 was taken and diluted with water at a 1:20 ratio, thus obtaining a cosmetic form of the product.

Next, 5 standardized tufts of 20 cm discolored hair were treated with 1 g of the cosmetic form described above, between washing intervals using a 10% lauryl ether sodium sulfate (LESS) solution, followed by rinsing.

The treated tufts were compared with tufts that had not undergone the treatment in the combability test, using a MTT 170 dynamometer manufactured by Dia-Stron Ltd, England.

Figure 2A:
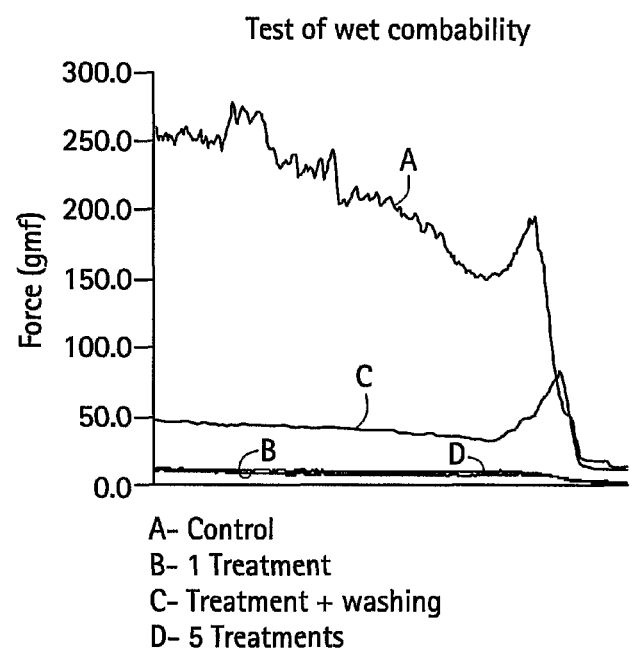
FIGS. 2A-B show the effect a lamellar gel composition according to one embodiment on wet combability in standardized colored hair tufts following washing (A) and following irradiation (B).
Figure 2B:
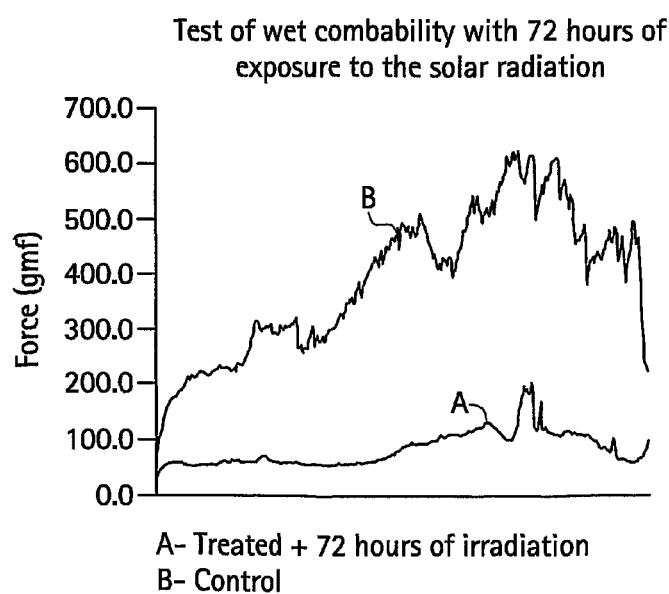

The results obtained are given in FIGS. 2A and 2B and demonstrate that the composition of the invention has provided a significant reduction in the combing strength, therefore making it easier to comb the hair.

All dates are related to the media for 5 tufts.

Example 4

Fiber Stretching Test and Determination of the Resistance with 5 and 20% Stress and of the Breaking Point 40 hair shafts taken from the hair tufts treated in Example 3, plus 40 untreated hair shafts that used as standard hair, were selected and tested.

The hair shafts were submitted to a tensile strength essay at 5%, 20% and breaking point of the fiber, with the equipment Mitutoyo LSM-5000 to measure the diameter and a MTT 670 dynamometer MTT 670 manufactured by the company Dia-Stron Ltd. for the work.

Figure 3A:
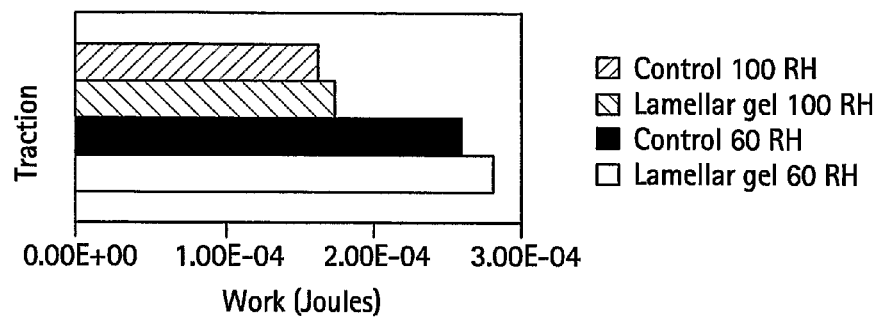
FIGS. 3A-C show results of fiber stretching test with a tensile strength 5% (A), 20% (B), and breaking point of the fiber (C) using a lamellar gel composition according to one embodiment.
Figure 3B:
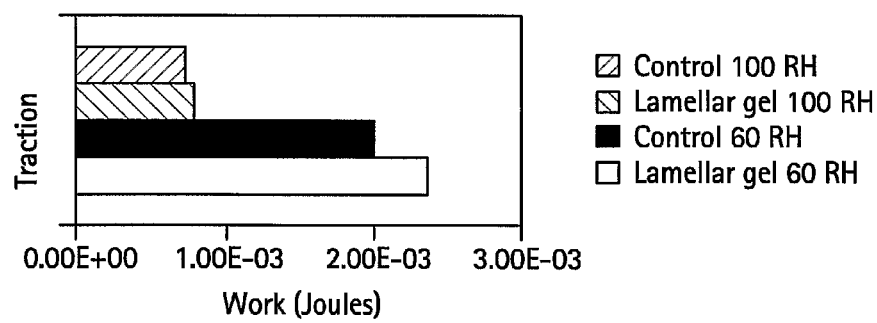
Figure 3C:
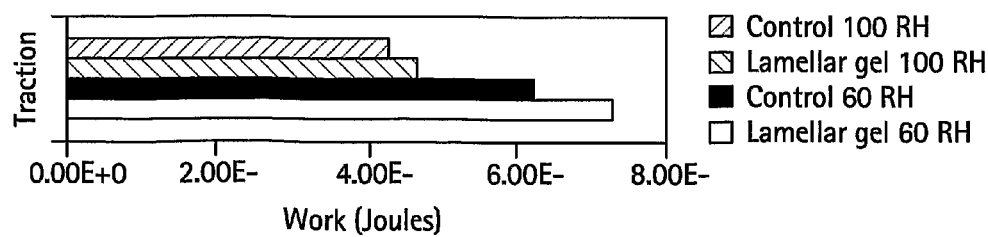

The results obtained are shown in Table 1 below and in the graphs of FIGS. 3A, 3B and 3C, demonstrating that the lamellar gel composition of the present invention has provided a tensile strength increase of the fiber in the 3 aspects evaluated, with 60% and 100% relative humidity (RH).

TABLE 1

RESULTS OF THE TEST OF EXAMPLE 4

|  | 5% Work Joules | 20% Work Joules |  |
| --- | --- | --- | --- |
|  |  |  | Breaking point work 60 RH Joules |
| Treated | 2.81E−04 | 2.26E−03 | 7.27E−03 |
| Control | 2.60E−04 | 1.90E−03 | 6.24E−03 |
|  |  |  | Breaking point work 100 RH Joules |
| Treated | 1.74E−04 | 7.32E−04 | 4.65E−03 |
| Control | 1.62E−04 | 6.82E−04 | 4.26E−03 |

Example 5

Electronic Microscopy Fluorescence Essay

Three hair tufts treated according to Example 2, and three untreated control hair tufts were tested. Three randomly selected hair shafts of each of the hair tufts were treated with pigment rodamine B in order to check, via fluorescence microscopy, the effect of both superficial and deep restoration, and the recovery of the oxidative damages. The results are given in Table 2 below and in FIGS. 4A and 4B, wherein the higher the intensity of the fluorescence the higher the presence of cysteic acid, a product derived from the breakage of the cystein links present both on the surface and the cortex of the hair. The intensity of the fluorescence was measured both in the longitudinal segment, that represents superficial damage, and in the sectional segment, that represents deep damage in the cortex of the hair. The equipment used therefor was a fluorescence microscope manufactured by the company Leica, with No. 2.1 cubic filters.

TABLE 2

RESULTS OF THE TEST OF EXAMPLE 5

|  | Intensity ua |
| --- | --- |
| Transversal (superficial) |  |
| Treated | 42 |
| Control | 136 |

TABLE 2-continued

RESULTS OF THE TEST OF EXAMPLE 5

| | Intensity ua |
|---|---|
| Sectional (deep) | |
| Treated | 27 |
| Control | 156 |

Examples 6-12

Table 3 lists some Example Compositions of this invention

TABLE 3

| Ingredients | Ex. 6 | Ex. 7 | Ex. 8 | Ex. 9 | Ex. 10 | Ex. 11 | Ex. 12 | Phase |
|---|---|---|---|---|---|---|---|---|
| Prolipid 161* | 15 | 20 | 20 | 25 | 20 | 15 | 15 | B |
| Ceraphyl 70* | 8 | 5 | 0 | 0 | 0 | 0 | 8 | B |
| Ceraphyl ica* | 8 | 6 | 8 | 5 | 7 | 8 | 8 | B |
| Escalol HP* | 3 | 3 | 3 | 0 | 0 | 0 | 0 | B |
| Glycerine | 55 | 55 | 55 | 50 | 50 | 55 | 55 | A |
| Vital ET ® | 3.8 | 0 | 0 | 0 | 3.8 | 3.8 | 3.8 | C |
| Glycine | 0.4 | 0 | 0 | 0 | 0.4 | 0.4 | 0.4 | C |
| Arginine | 0.2 | 0 | 0 | 0 | 0.2 | 0.2 | 0.2 | B |
| Acetyl cystein | 0.2 | 0 | 0 | 0 | 0.2 | 0.2 | 0.2 | C |
| Lauryl lysine | 0.4 | 0 | 0 | 0 | 0.4 | 0.4 | 0.4 | C |
| Water | BAL | BAL | BAL | BAL | BAL | BAL | BAL | A |

*Prolipid 161 contains behenic alcohol (35%) + cetyl alcohol (35%) + hydroxyl ethyl cetearamidopropyldimmonium chloride (30%); Ceraphyl 70 is quaternium 70; Escalol HP is dimethylPARAmidopropyl laurdimmonium tosylate. Ceraphyl ICA is isocetyl alcohol; Vital ET ® is disodium lauriminodipropionate tocopheryl phosphate.

Procedure to orepare the example formulations:

(1) In a container, add Phase A, glycerine and water, heat to 75° C.

(2) In a separate container, mix phase B ingredient and heat to 75° C. and add it to phase A under agitation.

(3) Under agitation, cool the mixture to 40° C. and add phase C.

Evaluation Methods for Assessing Hair Mass Increase

Single fiber test method with optical microscopy:
Hair fibers were bleached in a commercial hair bleach product (Pure White by Clairol Professional, 30 volume) at pH 10 for 30 min and then used for hair mass increase evaluation.

1. Tape hair fibers on a microscope glass slide firmly.
2. Soak the glass slide in pH 10 hydrogen peroxide solution for 30 min. to bleach the hair. Then rinse and dry.
3. Cut ~0.7 cm long pieces of one fiber, tape it well on another glass slide.
4. Take pictures of the fiber near both sides of the tape edges as markers at 500× magnification.
5. Soak the fiber mounted on a glass slide (from step 4) in a 5% test solution for 10 min. Rinse and dry.
6. Take pictures again on the same sites and compare the hair size changes microscopically.

Gravimetric Method:
Measure single fiber weight, mg/mm, calculate an average number from tests of over 250 hair fibers.
1. Split a bleached hair tress into two groups, one group of hair fibers are treated with test formulation solution, rinse and dry. The other group remain untreated.
2. Cut each group of hair fibers into 10 cm length and weigh them on a micro balance and record the weight in milligram.
3. Count the number of hair fibers in each of the two groups and calculate the single fiber weight as mg/mm using the weigh data obtained in step 2, the number of hair fibers and the length of hair fiber, 100 mm.

Examples 13-17

A number of formulations containing the compositions within the scope of this invention were made and tested for mass increase effect on bleached hair fibers using single fiber test method with microscopy. For comparison purpose, some comparative formulations outside the scope of this invention were also tested. The formulations tested are listed in Table 4 and Table 5. All the formulations were tested in a 5% solution in water except 3% ALS was tested as it is. Each formulation was tested with fibers. The results of hair mass increase test are also listed in the same tables.

TABLE 4

| Ingredients | Ex. 13 | Ex. 14 | Ex. 15 | Comparative | Ex. 16 | Comparative | Comparative | Ex. 17 |
|---|---|---|---|---|---|---|---|---|
| Prolipid 161 | 15 | 15 | 15 | 15 | 15 | 0 | 15 | 15 |
| Ceraphyl 70 | 8 | 8 | 8 | 0 | 0 | 8 | 0 | 0 |
| Ceraphyl ica | 8 | 8 | 8 | 8 | 8 | 8 | 0 | 8 |
| Escalol HP | 3 | 3 | 3 | 0 | 0 | 3 | 0 | 0 |
| Escalol 567 | 1 | 1 | 1 | 0 | 0 | 1 | 0 | 0 |
| DC 2-8177 | 5.0 | 0 | 0 | 0 | 0 | 0 | 0 | 0 |
| Glycerine | 55 | 55 | 55 | 0 | 55 | 55 | 0 | 55 |
| Vital ET ® | 3.8 | 3.8 | 0 | 0 | 0 | 3.8 | 0 | 3.8 |
| Glycine | 0.4 | 0.4 | 0 | 0 | 0 | 0.4 | 0 | 0.4 |
| Arginine | 0.2 | 0.2 | 0 | 0 | 0 | 0.2 | 0 | 0.2 |
| Acetyl cystein | 0.2 | 0.2 | 0 | 0 | 0 | 0.2 | 0 | 0.2 |
| Lauryl lysine | 0.4 | 0.4 | 0 | 0 | 0 | 0.4 | 0 | 0.4 |
| Water | BAL to 100 | BAL to 100 | BAL | BAL | BAL | 3.8 | BAL | BAL |
| Mass increase of hair fiber | yes | yes | yes | no | yes | no | no | yes |

Escalol 567 is benzophenone-3.

TABLE 5

| Ingredients | Comparative | Comparative | Comparative | Comparative, 3% ALS |
|---|---|---|---|---|
| Prolipid 161 | 0 | 0 | 0 | 0 |
| Ceraphyl 70 | 0 | 8 | 0 | 0 |
| Ceraphyl ica | 0 | 0 | 0 | 0 |
| Escalol HP | 0 | 0 | 0 | 0 |
| Escalol 567 | 0 | 0 | 0 | 0 |
| Glycerine | 55 | 0 | 0 | 0 |
| Vital ET ® | 0 | 0 | 0 | 0 |
| Glycine | 0 | 0 | 0 | 0 |

TABLE 5-continued

| Ingredients | Comparative | Comparative | Comparative | Comparative, 3% ALS |
|---|---|---|---|---|
| Arginine | 0 | 0 | 0.4 | 0 |
| Acetyl cystein | 0 | 0 | 0 | 0 |
| Lauryl lysine | 0 | 0 | 0 | 0 |
| Water | BAL | BAL | BAL | BAL |
| Mass increase of hair fiber | no | no | no | no |

It can be seen from the results of hair mass increase test that the formulations within the scope of this invention containing fatty alcohol, cationic surfactant and glycol increase the hair mass of bleached damaged hair fibers whereas all the comparative formulations outside the scope of this invention show no effect on hair mass increase. Some microscope images of tested fibers before and after treatment in the 5% example formulations and also the comparative formulations were observed. The images showed that the hair fibers treated with formulations within the scope of this invention increase the hair mass compared with that before treatment whereas the hair fibers treated in the comparative formulations show no increase in hair mass.

Example 18

In this example, hair mass increases of bleached hair fibers after treatment with a selected inventive formulation were quantitatively determined using the gravity method measuring single fiber weight as mg/mm. The results are listed in Table 6. Percent weight loss of bleached hair fibers relative to the non bleached hair fibers before and after treatment are listed in Table 7. The results show that the inventive formulation recovered hair mass loss from 8.2% to 2.1% for hair bleached for 30 min., and from 9.3% to 1.0% for hair bleached for 1 hour.

TABLE 6

Hair Mass Changes Before and After Treatment with Formulation of Example 13

|  | Before treatment hair mass, mg/mm | After treatment hair mass, mg/mm |
|---|---|---|
| Normal hair | 0.0535 |  |
| 30 min. Bleached | 0.0491 | 0.0523 |
| 1 hour Bleach | 0.0485 | 0.0529 |

TABLE 7

Recovery of Hair Mass Loss by Treatment with Formulation of Example 13

|  | Before treatment Wt. % loss relative to unbleached hair | After treatment Wt. % loss relative to unbleached hair |
|---|---|---|
| 30 min. Bleached | 8.22 | 2.24 |
| 1 hour Bleach | 9.33 | 1.12 |

Example 19

Salon Test Results

The formulation of Example 14 was selected to test in a Salon for hair fullness, thickness and smoothness response. This was a half head test with one half of the head treated with a conditioning formulation containing 5% of the formulation of Example 14 and the other half of head was treated with a control formula. The formulation of Example 14 was incorporated into a conditioning formulation at a 5% level replacing the conditioning agent, cetrimonium chloride. As a control formula, the same conditioning formulation containing 2% cetrimonium chloride was also tested.

The conditioning formulation is listed in Table 8.

TABLE 8

Conditioning Formulation for Salon Test

| Ingredient | Example 19 | Control |
|---|---|---|
| Water | 90.65 | 90.65 |
| Natrosol 250 HHR | 0.75 | 0.75 |
| EDTA Na2 | 0.10 | 0.10 |
| Example 14 | 5.00 | 0 |
| Centrimonium chloride | 0 | 2.00 |
| Lanette O | 2.00 | 2.00 |
| Arlacel 165 | 1.00 | 1.00 |
| Liquid Germall Plus | 0.50 | 0.50 |

Five panelists having bleached and/or colored hair participated in the Salon test. First the hair was washed with a shampoo product and rinsed well, towel dried and treated with the two formula in Table 8 on each half of the head. After the hair dry, the hair is observed for hair thickness or fullness and felt for smoothness.

The test results are listed in Table 9 and 10 for hair fullness and smoothness response respectively.

TABLE 9

Hair Thickness/Fullness Response

|  | Hair Thicker/Fullness Score* |  | Beginning Hair |
|---|---|---|---|
|  | Example 19 | Control | Type/Texture |
| Panelist 1 | 3.0 | 2.0 | Bleached/thin |
| Panelist 2 | 3.0 | 3.0 | Colored/thin |
| Panelist 3 | 3.0 | 2.0 | Bleached/thin |
| Panelist 4 | 3.0 | 2.5 | Colored/thin |
| Panelist 5 | 4.0 | 3.0 | Colored/thin |
| Average | 3.2 | 2.5 |  |

*Scoring: of hair fullness and thickness is 5 = excellent body (fullness/bounce); 4 = good; 3 = average; 2 = poor; 1 = no body

TABLE 10

Hair Smoothness Response

|  | Hair Thicker/Fullness Score* |  | Beginning Hair |
|---|---|---|---|
|  | Example 19 | Control | Type |
| Panelist 1 | 4.0 | 3.0 | Bleached |
| Panelist 2 | 4.0 | 3.5 | Colored |
| Panelist 3 | 3.5 | 3.5 | Bleached |
| Panelist 4 | 4.0 | 3.0 | Colored |
| Panelist 5 | 4.0 | 3.0 | Colored |
| Average | 3.9 | 3.2 |  |

*Scoring: 5 - extremely smooth and silky; 4 - smooth/silky; 3 - slightly smooth, 2 - slightly raspy, 1 - not smooth extremely raspy.

Four out of 5 panelist agreed that after using the formula of the invention, the hair was fuller, thicker, heavier than the control formula. Three out of 5 panelists agreed that after using the formula of the invention, the hair was smoother than the control formula.

Example 20

Glycerin (62%), Hydroxyethyl Cetearamidopropyldimonium Chloride; Behenyl Alcohol; Cetearyl Alcohol (ProLipid 161) (10%); Polyquaternium 55 (Styleze W-20) (10%); Cyclopentasiloxane; Dimethiconol (10%); Ceteareth-20 (8%).

This Example formed a lamellar oil-in-glycol polymer gel which provided shine as well as humidity and color protection when applied to a keratinous substrate and improved the substrates hydrophobicity.

One skilled in the art will readily know how to evaluate, by means of the teachings contained in the text and in the examples given herein, the advantages of the invention, and propose equivalent variations and alternatives for embodiments thereof, without however departing from the scope of the invention, as defined in the accompanying claims.

The invention claimed is:

1. A lamellar oil-in-glycol gel, characterized by comprising (a) at least one glycol selected from the group consisting of butylene glycol, propylene glycol, 1,2,3-propanetriol and mixtures thereof, (b) at least one fatty alcohol selected from the group consisting of isocetyl, stearyl, cetyl, behenic, oleic, linoleic alcohols, and mixtures thereof and (c) a cationic surfactant comprising a mixture of hydroxy ethyl cetearamidopropyldimmonium chloride, dimethylPABAmidopropyl laurdimmonium tosylate and quaternium 70, wherein the amount of glycol ranges from about 30 and 90% by weight, the amount of fatty alcohol ranges from about 0.1 to about 40% by weight, and the amount of cationic surfactant ranges from about 0.001 to about 30% by weight in relation to the total weight of the composition.

2. A lamellar oil-in-glycol gel in accordance with claim 1 further comprising (d) at least one benefit agent.

3. A lamellar oil-in-glycol gel in accordance with claim 2, characterized in that the benefit agent is chosen among amino acids, its salts, esters and/or acyl derivatives, alkyl substituted amino acids, its salts and/or alkyl substituted imino acids, silicones, or mixtures thereof.

4. A lamellar oil-in-glycol gel in accordance with claim 3, characterized in that the amino acid is chosen among glycine, lysine lauroil, arginine HCl, N-acetyl cystein, or mixtures thereof.

5. A lamellar oil-in-glycol gel in accordance with claim 4, characterized in that the amount of amino acid ranges from about 0.001 to about 20% by weight in relation to the total weight of the composition.

6. A lamellar oil-in-glycol gel in accordance with claim 3, characterized in that the alkyl substituted amino acid is disodium lauriminodipropionate tocopheryl phosphate.

7. A lamellar oil-in-glycol gel in accordance with claim 3, characterized in that the amount of alkyl substituted amino acid ranges from about 0.001 to about 30% by weight in relation to the total up weight of the composition.

8. A lamellar oil-in-glycol gel in accordance with claim 3, characterized in that the silicone is chosen from among siloxane polymers terminated with functional amino groups.

9. A lamellar oil-in-glycol gel in accordance with claim 8, characterized in that the silicone is prepared with non-ionic emulsifiers selected from $C_{12-14}$ alkoxylated alcohols and amines.

10. A lamellar oil-in-glycol gel in accordance with claim 3, characterized in that the amount of silicone ranges from about 0.001 to about 30% by weight in relation to the total weight of the composition.

11. A lamellar oil-in-glycol gel in accordance with claim 1, characterized in that its melting point is about 36° C. to about 46° C.

12. A cosmetic product characterized by comprising the lamellar oil-in-glycol gel according to claim 1 and keratinous substrata compatible excipients.

13. A cosmetic treatment method, characterized by comprising the application of a lamellar oil-in-glycol gel according to claim 1 onto keratinous substrata.

14. A lamellar oil-in-glycol gel in accordance with claim 1 wherein the amount of cationic surfactant ranges from about 0.2 to about 30% by weight in relation to the total weight of the composition.

15. A process for the preparation of a lamellar oil-in-glycol gel, as defined in claim 1, characterized by comprising the steps of (1) heating separately the at least one glycol and the at least one fatty alcohol in combination with the cationic surfactant to a temperature of about 65° C. to about 85° C., (2) adding the fatty alcohol with the cationic surfactant to the glycol under agitation, (3) keeping the agitation until the mixture is homogenized and (4) cooling the homogenized mixture to a temperature of about 30° C. to about 50° C.

16. The process in accordance with claim 15 further comprising the step of (5) adding at least one benefit agent under agitation until a homogeneous product is obtained.

* * * * *